United States Patent
Hoxmeier

(10) Patent No.: US 6,225,390 B1
(45) Date of Patent: May 1, 2001

(54) OIL GEL FORMULATIONS CONTAINING POLYSTYRENE-POLYDIMETHYLSILOXANE OR POLYETHYLENE-POLYDIMETHYLSILOXANE BLOCK COPOLYMERS DISSOLVED IN SILOXANE MONOMERS

(75) Inventor: Ronald James Hoxmeier, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/307,285

(22) Filed: May 7, 1999

Related U.S. Application Data

(60) Provisional application No. 60/084,707, filed on May 8, 1998.

(51) Int. Cl.$^7$ .......................... C08K 5/54; C08K 5/5415; C08G 77/42
(52) U.S. Cl. .......................... 524/261; 524/267; 524/588; 525/106; 528/14; 528/25; 528/33
(58) Field of Search ..................................... 524/261, 267, 524/588; 525/106; 528/14, 25, 33

(56) References Cited

U.S. PATENT DOCUMENTS

| | | | |
|---|---|---|---|
| 4,123,409 | * | 10/1978 | Kaelble . |
| 5,079,300 | * | 1/1992 | Dubrow et al. ................. 525/106 |
| 5,728,469 | * | 3/1998 | Mann et al. .................... 428/416 |
| 5,880,210 | * | 3/1999 | Schulz, Jr. et al. ............ 524/731 |

OTHER PUBLICATIONS

Dow Corning Products Catalog: internet.*

* cited by examiner

*Primary Examiner*—Robert Dawson
*Assistant Examiner*—Jeffrey B. Robertson
(74) *Attorney, Agent, or Firm*—Donald F. Haas

(57) ABSTRACT

This invention is a silicone oil gel composition which is comprised of a silicone block copolymer selected from the group consisting of polyethylene-polydimethylsiloxane block copolymers and polystyrene-polydimethylsiloxane block copolymers wherein the overall number average molecular weight is from 2000 to 251,000, the polystyrene content (PSC) is 40% or less by weight, the polystyrene block number average molecular weight is from 1000 to 30,000, and the polyethylene number average block molecular weight is from 1000 to 20,000, the polydimethylsiloxane number average molecular weight is from 1000 to 250,000, wherein the block copolymer is dissolved in a silicone oil which is a cyclic or linear siloxane monomer. Preferred siloxane monomers for use herein are $(Me_2SiO)_3$, $(Me_2SiO)_4$, and $(Me_2SiO)_5$.

17 Claims, No Drawings

OIL GEL FORMULATIONS CONTAINING POLYSTYRENE-POLYDIMETHYLSILOXANE OR POLYETHYLENE-POLYDIMETHYLSILOXANE BLOCK COPOLYMERS DISSOLVED IN SILOXANE MONOMERS

This application claims the benefit of U.S. Provisional Application No. 60/084,707, filed May 8, 1998, the entire disclosure of which is hereby incorporated by reference

FIELD OF THE INVENTION

This invention relates to oil gel compositions for use in cosmetics and pharmaceutical products, cable packing, etc. More particularly, this invention relates to such compositions containing polystyrene-polydimethylsiloxane or polyethylene-polydimethylsiloxane block copolymers and which utilize siloxane monomers as the oil.

BACKGROUND OF THE INVENTION

Silicone gel compositions have been used in a variety of products, including sunscreen gels, moisturizing creams, antiperspirant creams, liquid foundations, and hair gels. Known silicone gel compositions include compositions comprised of silicone oil and wax, silicone oil and silica, and silicone oil and polyoxyalkylene-containing organopolysiloxanes, such as described in European Published Patent Application No. 0,568,102. That application identifies a number of possibilities for components useful as the silicone oil including low and high viscosity diorganopolysiloxanes, including polydimethylsiloxane, cyclic siloxanes, cyclic siloxane solutions of polydimethylsiloxane gums, etc.

Linear block copolymers of polystyrene and polydimethylsiloxane have been synthesized, both by graft and block copolymerization. In block copolymerization of such linear polymers, polystyrene is produced by anionic polymerization with an organo lithium initiator and the living polymer (PS-Li+) created thereby is reacted with hexamethylcyclotrisiloxane, $(Me_2SiO)_3$, in the presence of a polar promoter wherein a block of polydimethylsiloxane grows on the end of the living vinyl aromatic hydrocarbon polymer block. U.S. Pat. No. 5,618,903 describes a block copolymer which is an anionically polymerized block copolymer which is comprised of at least one block of high density (HDPE) polyethylene and at least one block of a polysiloxane, e.g., polydimethylsiloxane. These polymers are useful for impact modification of engineering thermoplastics, flow promoters, and forming coatings with low energy surfaces but have not been used or suggested for use as components of oil gels.

SUMMARY OF THE INVENTION

This invention is a silicone oil gel composition which is comprised of a silicone block copolymer selected from the group consisting of polyethylene-polydimethylsiloxane block copolymers and polystyrene-polydimethylsiloxane block copolymers wherein the overall number average molecular weight is from 2000 to 251,000, the polystyrene content (PSC) is 40% or less by weight, the polystyrene block number average molecular weight is from 1000 to 30,000, and the polyethylene number average block molecular weight is from 1000 to 20,000, the polydimethylsiloxane number average molecular weight is from 1000 to 250,000, wherein the block copolymer is dissolved in a silicone oil which is a cyclic or linear siloxane monomer. Preferred siloxane monomers for use herein are $(Me_2SiO)_3$, $(Me_2SiO)_4$, and $(Me_2SiO)_5$.

DETAILED DESCRIPTION OF THE INVENTION

The polyethylene-polydimethylsiloxane and polystyrene-polydimethylsiloxane block copolymers of this invention and the method of making them are fully described in U.S. Pat. No. 5,618,903, which is herein incorporated by reference. In block copolymerization of such linear polystyrene-polydimethylsiloxane polymers, polystyrene is produced by anionic polymerization with an organo lithium initiator and the living polymer (PS-Li+) created thereby is reacted with hexamethylcyclotrisiloxane, $(Me_2SiO)_3$, in the presence of a polar promoter wherein a block of polydimethylsiloxane grows on the end of the living vinyl aromatic hydrocarbon polymer block.

In general, when solution anionic techniques are used, polymers of anionically polymerizable monomers are prepared by contacting the monomer to be polymerized simultaneously or sequentially with an anionic polymerization initiator such as Group IA metals, their alkyls, amides, silanolates, naphthalides, biphenyls and anthracenyl derivatives. It is preferable to use an organo alkali metal (such as sodium or potassium) compound in a suitable solvent at a temperature within the range from −150° C. to 300° C. preferably at a temperature within the range from 0° C. to 100° C. Particularly effective anionic polymerization initiators are organo lithium compounds having the general formula:

$$RLi_n$$

wherein R is an aliphatic, cycloaliphatic, aromatic or alkyl-substituted aromatic hydrocarbon radical having from 1 to 20 carbon atoms; and n is an integer of 1–4.

In general, any of the solvents known in the prior art to be useful in the preparation of such polymers may be used. Suitable solvents, then, include straight- and branched-chain hydrocarbons such as pentane, hexane, heptane, octane and the like, as well as, alkyl-substituted derivatives thereof; cycloaliphatic hydrocarbons such as cyclopentane, cyclohexane, cycloheptane and the like, as well as, alkyl-substituted derivatives thereof; aromatic and alkyl-substituted derivatives thereof; aromatic and alkyl-substituted aromatic hydrocarbons such as benzene, naphthalene, toluene, xylene and the like; hydrogenated aromatic hydrocarbons such as tetralin, decalin and the like; linear and cyclic ethers such as methyl ether, methyl ethyl ether, diethyl ether, tetrahydrofuran and the like.

Ethylene may be polymerized as described above with the addition that it is usually best to include a promoter, such as a diamine, to facilitate the reaction. Examples of these amines which include but are not limited to follow: N,N,N',N'-tetramethylmethylenediamine (TMMDA), N,N,N',N'-tetramethylethylenediamine (TMEDA), N,N,N',N'-tetraethylethylenediamine (TEEDA), N,N,N',N'-tetramethyl-1,3-propanediamine (TMPDA), N,N,N',N'tetramethyl-1,4-butanediamine (TMBDA), dipiperidinomethane (DIPIM), 1,2dipiperidinoethane (DIPIE), 1,8-bis(dimethylamino)naphthalene, N,N,N',N'tetramethyl-o-phenylenediamine (TMOPDA), 1,2-dipyrolidinoethane (DIPIP), 1,3dipiperidinopropane (DIPIP), 1,2-bis(2.6-dimethylpiperidino)cyclohexane (BDMPC), sparteine, and the like.

The ethylene polymerization reaction can be carried out at 0° C. to 100° C. preferably 25° C. to 60° C. The ethylene pressure can be from 10 psig to 1000 psig, preferably 100 to 500 psig, The polymerization time can run from 10 minutes to 2 hours, preferably 30 minutes to 1 hour.

When the polymerization of the ethylene is complete, living polyethylene blocks are present in the polymerization mixture. These are perfectly linear polyethylene-alkyllithiums. These living polyethylenes can then be reacted with cyclic siloxane monomers $(R_1R_2SiO)_n$, where n=3–10, $R_1$ and $R_2$=alkyl ($C_1$–$C_{20}$), alkenyl ($C_2$–$C_{20}$), hydrogen, benzyl or phenyl (including alkyl substituted aromatics and polycyclics) and $R_1$ and $R_2$ can be the same or different. Specific siloxane monomers include $(Me_2SiO)_3$, $(MeHSiO)_3$, $(Me_2SiO)_4$, $(Me_2SiO)_5$, $(MeHSiO)_4$, $(MeHSiO)_5$, $(Ph_2SiO)_3$, $(Ph_2SiO)_4$, $(Ph_2SiO)_5$, $(PhHSiO)_4$, $(PhHSiO)_5$, $(PhHSiO)_3$, $(vinylmethylSiO)_4$, $(vinylmethylSiO)_5$, $(vinylHSiO)_3$, $(vinylHSiO)_4$, $(vinylHSiO)_5$, $(vinylmethylSiO)_3$, $(PhMeSiO)_3$, $(PhMeSi)_4$, $(PhMeSiO)_5$. Mixtures of monomers can also be used. When a polydimethylsiloxane block is desired with RLi initiator, the monomer is preferably hexamethylcyclotrisiloxane (D3) or octamethylcyclotetrasiloxane (D4).

This polymerization is carried out in the presence of a polar promoter, including, but not limited to, the promoter present during the ethylene polymerization step. Additional promoter can be added. Such promoters include but are not limited to diethers and/or diamines, such as diethylglyme andor TMEDA, cyclic ethers such as tetrahydrofuran, and any promoter known to be useful in anionic polymerizations. Its purpose is to decrease the reaction time of the D3 polymerization. Preferably, this reaction is carried out at a temperature of from 30° C. to 120° C., the concentration of the cyclic siloxane monomer (described herein in terms of hexamethylcyclotrisiloxane) is from 1 to 80 percent by weight, and the amount of promoter used ranges from 100 ppm to essentially 100 percent by weight (i.e. the polar promoter is used as solvent). The temperature range is important because higher temperatures cause more rapid reaction. The promoter concentration range is important for the same reason. The reaction may be carried out at up to 80 weight percent solids, preferably 10 to 80 percent. This is advantageous because higher solids offer economic advantages because less solvent is necessary.

The living block copolymer can be recovered directly to give PE-PDMS-O-Li$^+$(or PS-PDMS-O-Li$^+$ when the first block is polymerized from styrene) which is a living polymer and has not been terminated. One could manufacture and sell the living polymer itself to others that could then react it to form other polymers and/or add other functionalities. Termination of the polymer may be achieved by several conventional means. If desired, the polymer can be capped with $R_3R_4R_5$-SiX, e.g., to give PE-PDMS-SiR$_3$R$_4$R$_5$ (or PS-PDMS-SiR$_3$R$_4$R$_5$), where the R's can be alkyl, alkenyl ($C_2$–$C_{20}$, preferably a vinyl group because of its high reactivity), amino, alcohol, carboxylate, and other hetero atom containing functionalities, phenyl, benzyl, hydrogen, and the like, and can be the same or different, and X is halogen, preferably chlorine, or alkoxide, preferably $C_1$–$C_{20}$. It can be protonated with, e.g., acetic acid, to give PE-PDMS-OH (or PS-PDMS-OH). It can also be coupled with, e.g., SiCl$_4$, Me$_2$SiCl$_2$, HSi(OMe)$_3$ with coupling agent functionalities from 2 to about 12 to give (PE-PDMS)$_n$ (or (PS-PDMS)$_n$), where n=the number of coupling agent functionalities. The coupling or capping reaction can be carried out from 40 to 100° C. for 5 minutes to 1 hour, preferably 70 to 100° C. for about 10 to 15 minutes.

The block copolymers of this invention have an overall number average molecular weight of from 2000 to 251,000, preferably from 3000 to 100,000. The PS-PDMS block copolymers have a PSC of 40% or less, preferably 30% or less, by weight. The polyethylene blocks have number average molecular weights of from 1000 to 20,000, and most preferably from 1000 to 5000. The number average molecular weights of the polydimethylsiloxane blocks vary from 1000 to 250,000, preferably 1000 to 100,000. The number average molecular weights of the polystyrene blocks vary from 1000 to 30,000, preferably 1000 to 15,000.

The siloxane oil gel compositions of the present invention utilize the above block copolymers as the gelation agent portion of the composition. The oil or solvent portion of the compositions may be comprised of a cyclic siloxane such as $(R_1R_2SiO)_n$, where n=3–10, $R_1$ and $R_2$ =alkyl ($C_1$–$C_{20}$), alkenyl ($C_2$–$C_{20}$), hydrogen, benzyl or phenyl (including alkyl substituted aromatics and polycyclics) and $R_1$ and $R_2$ can be the same or different. Specific cyclic siloxane monomers include $(Me_2SiO)_3$, $(MeHSiO)_3$, $(Me_2SiO)_4$, $(Me_2SiO)_5$, $(MeHSiO)_4$, $(MeHSiO)_5$, $(Ph_2SiO)_3$, $(Ph_2SiO)_4$, $(Ph_2SiO)_5$, $(PhHSiO)_4$, $(PhHSiO)_5$, $(PhHSiO)_3$, $(vinylmethylSiO)_4$, $(vinylmethylSiO)_5$, $(vinylHSiO)_3$, $(vinylHSiO)_4$, $(vinylHSiO)_5$, $(vinylmethylSiO)_3$, $(PhMeSiO)_3$, $(PhMeSi)_4$, $(PhMeSiO)_5$. Mixtures of monomers can also be used. Linear siloxane monomers may also be used, e.g., Me(Me$_2$SiO)$_n$SiMe$_3$ where n=1 to 15. Preferred monomers for use herein are hexamethylcyclotrisiloxane (D3), octamethylcyclotetrasiloxane (D4), and decamethylcyclopentasiloxane (D5).

The block copolymers are mixed into the oil by dissolving the block copolymer in the cyclic monomers (or linear oligomers) at 90 to 200° C. for 1 to 2 hours.

The siloxane oil gel compositions of this invention are useful in cosmetic pharmaceutical compositions, cable filling application, etc. These compositions flow very easily at greater than 100° C. and set up (gel) at 25 to 50° C. (or lower). Thus, they are easily recyclable.

EXAMPLES

Three different cyclic siloxane monomer oils were used to dissolve a variety of siloxane polymers. They were hexamethylcyclotrisiloxane (D3), octamethylcyclotetrasiloxane (D4), and decamethylcyclopentasiloxane (D5). They were dissolved by heating at 90 to 200° C. for 1 to 2 hours, then cooled to room temperature at which point gelation occurred.

The results are shown in Table 1. PS indicates a polystyrene block. PDMS is polydimethylsiloxane. PE is polyethylene. PI is polyisoprene. EP is hydrogenated polyisoprene. PDPS is polydiphenylsiloxane. SEBS is a standard hydrogenated styrene-butadiene-styrene block copolymer. Polymer 10 had a high molecular weight (HMW) polyethylene block. Polymers 9 and 11 are graft copolymers rather than block copolymers. It can be seen that only the polymers that are within the scope of this invention, Polymers 1, 4, and 6 form a gel.

TABLE 1

$D_3$, $D_4$, $D_5$ Si-Oil Gels

| Solvent | Polymer | Polymer Type & Description | % wt | GEL | Polymer Dissolution Conditions (T/t*) |
|---|---|---|---|---|---|
| D4 | 1 | PS-PDMS-PS 6K-68K-6K (15% PSC) | 10% | GEL (grav. flow 5 min.) | 160° C./1 hr |
| D4 | 1 | PS-PDMS-PS 6K-68K-6K (15% PSC) | 15% | GEL (grav. flow 1 hr) | 160° C./1 hr |
| D4 | 2 | PS-EP-PDMS 3K-0.5K-5K | 10% | Insoluble | 175° C./2 hrs |
| D4 | 3 | SEBS | 10% | Insoluble | 175° C./2 hrs |
| D4 | None | — | 0% | No GEL | 175° C./2 hrs |
| D4 | 4 | PS-PDMS-PS 8K-32K-8K (33% PSC) | 5% | GEL (slumps in 4 hrs) (grav. flow in 8 hrs) | 170° C./2 hrs |
| D3 | 4 | PS-PDMS-PS 8K-32K-8K (33% PSC) | 5% | Crystalline GEL | 90° C./2 hrs |
| D4 | 5 | PS-PDMS-PS 14K-32K-14K (50% PSC) | 5% | Insoluble | 170° C./2 hrs |
| D4 | 6 | PE-PDMSLi 3K-3K | 5% | GEL (grav. flow in 4 hrs) | 160° C./1 hr |
| D5 | 6 | PE-PDMSLi 3K-3K | 15% | GEL (grav. flow in 1–2 days) | 160° C./1 hr |
| D5 | 6 | PE-PDMSLi 3K-3K | 5% | GEL (grav. flow in 1–2 days) | 160° C./1 hr |
| D5 | 6 | PE-PDMSLi 3K-3K | 20% | GEL (grav. flow in >2 days) | 160° C./2 hrs |
| D5 | 7 | PE-PDMS-PDPSLi 0.6K-3.6K-0.6K | 10% | Insoluble | 175° C./2 hrs |
| D5 | 8 | PE-PDMSLi 0.6K-3.6K | 10% | Insoluble | 175° C./2 hrs |
| D5 | 9 | $(C_{18})_x$PDMS | 10% | Insoluble | 175° C./2 hrs |
| D5 | 10 | HMW PE + PDMS | 10% | Insoluble | 175° C./2 hrs |
| D5 | 11 | $(PE)_x$-g-PDMS | 10% | Insoluble | 175° C./2 hrs |
| D5 | 12 | PS-PI-PDMS 8K-12K-60K | 10% | Insoluble | 175° C./2 hrs |
| D5 | 13 | PS-EP-PDMS 8K-12K-60K | 10% | Insoluble | 175° C./2 hrs |
| D5 | 14 | PS-PDMS 8K-60K (12% PSC) | 10% | Insoluble | 175° C./2 hrs |

*T = temperature, t = time
**D3 solidifies @ ~60° C.

I claim:

1. A silicone oil gel composition, comprising:
   a silicone oil which is a cyclic or linear siloxane monomer; and
   a silicone block copolymer which is dissolved in the silicon oil, wherein the silicone block copolymer is selected from the group consisting of polyethylene-polydimethylsiloxane block copolymers and polystyrene-polydimethylsiloxane block copolymers wherein the overall number average molecular weight is from 2000 to 251,000, the polystyrene content is 40% or less by weight, the polystyrene block number average molecular weight is from 1000 to 30,000, the polyethylene block number average molecular weight is from 1000 to 20,000, and the polydimethylsiloxane block number average molecular weight is from 1000 to 250,000.

2. The composition of claim 1 wherein the overall number average molecular weight is 3000 to 100,000 and the polystyrene content is 30% or less.

3. The composition of claim 2 wherein the polydimethylsiloxane block number average molecular weight is 1000 to 100,000.

4. The composition of claim 3 wherein the silicone block copolymer comprises the polystyrene block.

5. The composition of claim 1 wherein the silicone oil is a cyclic siloxane monomer.

6. The composition of claim 5 wherein the cyclic siloxane monomer is selected from the group consisting of $(R_1R_2SiO)_n$ where n=3–10, $R_1$ and $R_2$ are $C_1$–$C_{20}$ alkyl, $C_2$–$C_{20}$ alkenyl, hydrogen, or benzyl, and may be the same or different.

7. The composition of claim 6 wherein the cyclic siloxane monomer is selected from the group consisting of hexamethylcyclotrisiloxane, octamethylcyclotetrasiloxane, and decamethylcyclopentasiloxane.

8. A silicone oil gel composition, comprising:
   a silicone oil which is a cyclic or linear siloxane monomer; and
   a silicone block copolymer which is dissolved in the silicon oil, wherein the silicone block copolymer is selected from the group consisting of polyethylene-polydimethylsiloxane block copolymers and polystyrene-polydimethylsiloxane block copolymers wherein the overall number average molecular weight is from 3,000 to 100,000, the polystyrene content is 30% or less by weight, the polystyrene block number average molecular weight is from 1,000 to 30,000, the polyethylene block number average molecular weight is from 1,000 to 20,000, and the polydimethylsiloxane block number average molecular weight is from 1,000 to 100,000.

9. The composition of claim 8 wherein the silicone oil is a cyclic siloxane monomer.

10. The composition of claim 9 wherein the cyclic siloxane monomer is selected from the group consisting of $(R_1R_2SiO)_n$ where n=3–10, $R_1$ and $R_2$ are $C_1$–$C_{20}$ alkyl, $C_2$–$C_{20}$ alkenyl, hydrogen, or benzyl, and may be the same or different.

11. The composition of claim 9 wherein the cyclic siloxane monomer is selected from the group consisting of hexamethylcyclotrisiloxane, octamethylcyclotetrasiloxane, and decamethylcyclopentasiloxane.

12. A silicone oil gel composition, comprising:
   a silicone oil which is a cyclic or linear siloxane monomer; and
   a polyethylene-polydimethylsiloxane block copolymer wherein the overall number average molecular weight is from 2,000 to 251,000, the polyethylene block number average molecular weight is from 1,000 to 20,000, and the polydimethylsiloxane block number average molecular weight is from 1,000 to 250,000.

13. The composition of claim 12 wherein the overall number average molecular weight is 3000 to 100,000.

14. The composition of claim 13 wherein the polydimethylsiloxane block number average molecular weight is 1000 to 100,000.

15. The composition of claim 14 wherein the silicone oil is a cyclic siloxane monomer.

16. The composition of claim 15 wherein the cyclic siloxane monomer is selected from the group consisting of $(R_1R_2SiO)_n$ where n=3–10, $R_1$ and $R_2$ are $C_1$–$C_{20}$ alkyl, $C_2$–$C_{20}$ alkenyl, hydrogen, or benzyl, and may be the same or different.

17. The composition of claim 16 wherein the cyclic siloxane monomer is selected from the group consisting of hexamethylcyclotrisiloxane, octamethylcyclotetrasiloxane, and decamethylcyclopentasiloxane.

* * * * *